Feb. 12, 1957 E. S. BOERNER Plant Pat. 1,564
ROSE PLANT
Filed April 23, 1956
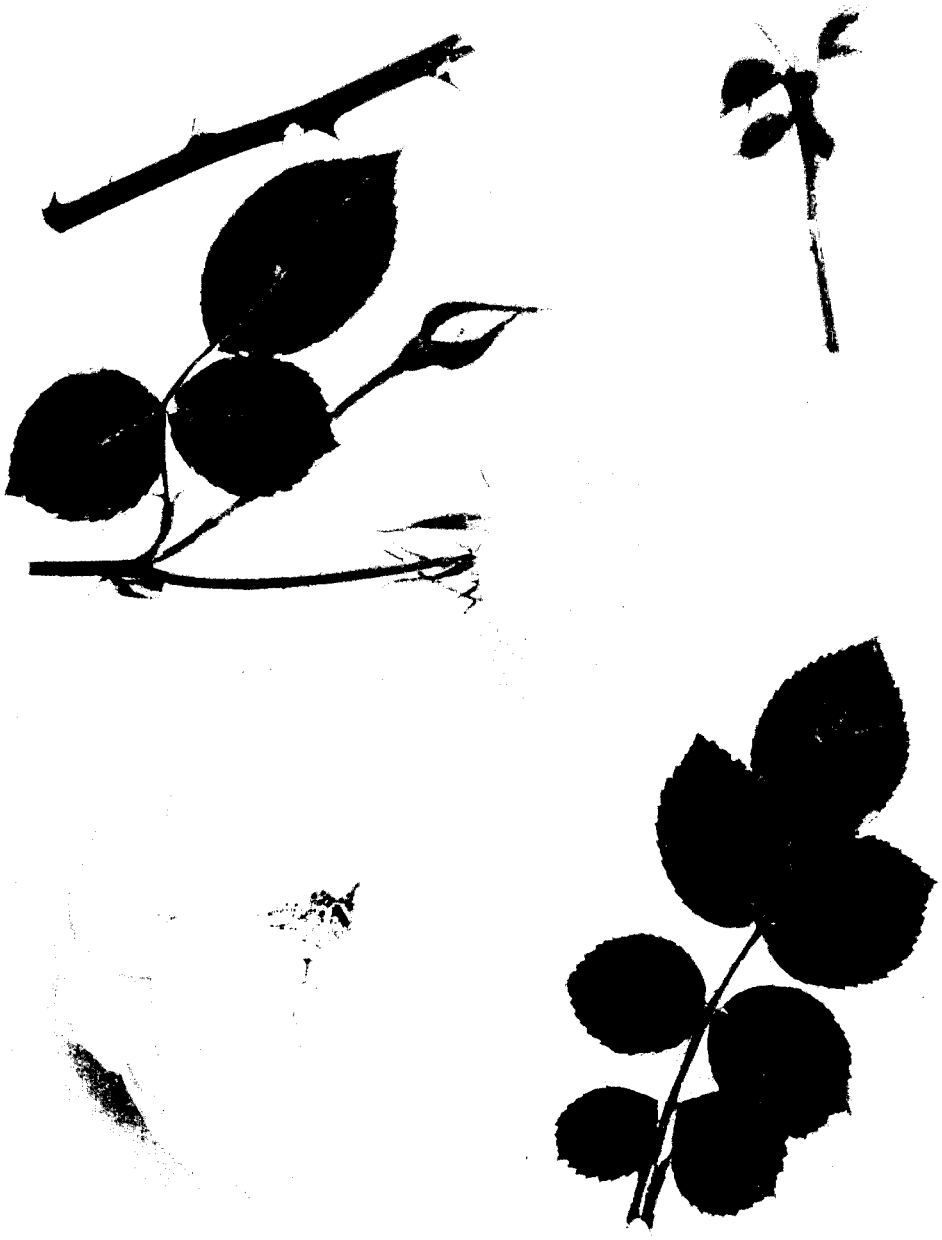
Inventor.
E. S. Boerner
By: Robbins & Robb
Attorneys.

United States Patent Office

Plant Pat. 1,564
Patented Feb. 12, 1957

1,564

ROSE PLANT

Eugene S. Boerner, Newark, N. Y., assignor to Jackson & Perkins Company, Newark, N. Y., a corporation of New York Application April 23, 1956, Serial No. 580,151

1 Claim. (Cl. 47—61)

The present invention relates to a new and distinct variety of rose plant of the large-flowered polyantha class, which was originated by me by crossing the variety "Fashion" (Plant Patent No. 789) with the variety "Fantasia" (Plant Patent No. 590), both of these parent varieties being Floribunda type varieties.

The primary object of this breeding was to produce a new rose variety which combines the large size of the flowers of "Fantasia" with the hardiness and vigor of the variety "Fashion," and otherwise to improve the flower form and growth of the variety "Fashion." This objective was fully achieved, as evidenced by the following unique combination of features which are outstanding in my new variety:

(1) Free flower production;

(2) Long-lasting flowers which are especially excellent for cut flowers;

(3) Larger flowers than those of the parent variety "Fashion";

(4) Greater flower petalage than that of either parent variety;

(5) The distinctive color of the half-open bud which is La France Pink, lightly overcast with white in the upper part of the petals, with Pinard Yellow overcasting the lower half of the petals; and (6) The distinctive general color tonality of the open flower which is Hermosa Pink, with the lower half of the petals lightly overcast with Marguerite Yellow, and the upper half of the petals lightly overcast with white.

The foregoing characteristics and distinctions definitely differentiate my new variety from its parents, as well as from all other varieties of its class of which I am aware, and asexual reproduction of the new variety by budding, as performed at Newark, New York, and also at Pleasanton, California, shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert Ridgway's Color Standards and Nomenclature:

Parentage: Seedling.
*Seed parent.*—"Fashion."
*Pollen parent.*—"Fantasia."
Classification:
*Botanic.*—Large-flowered polyantha.
*Commercial.*—Floribunda.

*Flower*

(Observations made from specimens grown in a greenhouse at Newark, New York, in the early part of April, and in late morning.)

Blooming habit: Recurrent—continuous.
Bud:
*Size.*—Medium.
*Form.*—Ovoid; is not affected by wet or hot weather.
*Color.*—When sepals first divide—Ivory Yellow, Plate 30, lightly overcast with Venetian Pink Plate 13. When petals begin to unfurl—Thulite Pink, Plate 26. When half-blown: inside of petals—La France Pink, Plate 1, lightly overcast with White, Plate 53, in the upper part of the petal, and with Pinard Yellow, Plate 4, overcasting the lower half of the petal; reverse of petals—Pale Pinkish Cinnamon, Plate 29, with Naphthalene Yellow, Plate 16, overcasting the lower half of the petal and with the outer edges of the petal La France Pink, Plate 1.
*Sepals.*—Slightly branched, with "hood" above bud; curl back when petals begin to unfurl. Color: inside—Light Grape Green, Plate 41; outside—Absinthe Green, Plate 31.
*Calyx.*—Color—Grass Green, Plate 31. Shape—pear. Size—long. Aspect—smooth. Odor when rubbed—none.
*Peduncle.* — Length — medium. Aspect — rough. Strength—erect; slender. Color—Spinach Green, Plate 5.
*Opening.*—Opens up well; is not affected by adverse weather conditions.
Bloom:
*Size.*—Medium. Average size when fully expanded—from 3½ inches to 4 inches.
*Borne.*—Several together and in irregular clusters.
*Stems.*—Medium length; strong.
*Form (when first open).*—Cupped. Permanence—flattens.
*Petalage.*—Double (full but open center). Number of petals under normal conditions—from 50 to 55.
*Color.*—Center of flower—La France Pink, Plate 1. Outer petals—Cameo Pink, Plate 26, lightly overcast with White, Plate 53. Base of petals (aiglet)—Pale Lumiere Green, Plate 17. Inside of petals—Hermosa Pink, Plate 1, with lower half of petal lightly overcast with Marguerite Yellow, Plate 30, and upper half of petal lightly overcast with White, Plate 53. Reverse of petals—Cameo Pink, Plate 26, lightly overcast with White, Plate 53. General tonality from a distance—La France Pink, Plate 1.
*Discoloration.*—General tonality at end of first day—La France Pink, Plate 1, lightly overcast with Hermosa Pink, Plate 1. Second day—Hermosa Pink, Plate 1, lightly overcast with White, Plate 53. Third day—Cameo Pink, Plate 26, lightly overcast with White, Plate 53.
Petals:
*Texture.*—Thick; leathery; is not affected by wet or hot weather.
*Appearance.*—Inside—shiny. Outside—satiny.
*Form.*—Oval.
*Arrangement.*—Irregular.
*Petaloids in center.*—Few; large.
*Persistence.*—Drop off cleanly.
*Fragrance.*—Strong. Nature—"Old Rose Perfume."
*Lasting quality.*—On the plant—very long. As cut flower—very long.

*Genital organs*

Stamens, anthers: Medium size; many; regularly arranged around styles. Color—Pinard Yellow, Plate 4.
Stamens, filaments (threads): Long. Color—Light Green Yellow, Plate 5.

Pollen: Color—Baryta Yellow, Plate 4.
Styles: Loosely separated; uneven length; long; thin.
Stigmas: Color—Martius Yellow, Plate 4.
Ovaries: All enclosed in calyx.
Hips: None.
Seeds: None.

*Plant*

Form: Bush.
Growth: Vigorous; bushy.
Foliage: Compound of 5 to 7 leaflets.
*Size.*—Medium.
*Quantity.*—Abundant.
*Color.*—New foliage: upper side—Oil Green, Plate 5, with serrations of Morocco Red, Plate 1; under side—Yellowish Oil Green, Plate 5, lightly overcast with Oxblood Red, Plate 1. Old foliage: upper side—Dark Dull Yellow Green, Plate 32; under side—Cress Green, Plate 31.
*Shape.*—Oval pointed.
*Texture.*—Upper side—glossy. Under side—smooth.
*Ribs and veins.*—Prominent.
*Edge.*—Serrated (saw-toothed).
*Serration.*—Single; small.
*Leaf stem.*—Color—Deep Dull Yellow Green (No. 1), Plate 32. Under side—rough.
*Stipules.*—Medium length; smooth.
Wood:
*New wood.*—Color—Garnet Brown, Plate 1. Bark—smooth.

*Old wood.*—Color—Empire Green, Plate 32. Bark—smooth.
Thorns:
*Thorns.*—Quantity: on main stalks from base—ordinary; on laterals from stalk—ordinary. Form—narrow base; short. Color (when young)—Carmine, Plate 1. Position—irregular.
*Prickles.*—Quantity: on main stalks—none; on laterals—none.
*Short needles.*—Quantity: on main stalks—none; on laterals—none.

I claim:

A new and distinct variety of rose plant of the large-flowered polyantha class, substantially as herein shown and described, characterized particularly as to novelty by its free flower production, its long-lasting flowers which are especially suitable for cut flowers, the large size of its flowers, the numerous petals of its flowers, the distinctive La France Pink general color tonality of its half-open buds, lightly overcast with white in the upper part of the petals and with Pinard Yellow overcasting the lower half of the petals, and the distinctive Hermosa Pink general color tonality of its open flowers, with the lower half of the petals lightly overcast with Marguerite Yellow, and the upper half of the petals lightly overcast with white.

No references cited.